United States Patent [19]

Kolts

[11] Patent Number: 4,658,081
[45] Date of Patent: Apr. 14, 1987

[54] PROPYLENE AND ETHYLENE SELECTIVITY WITH H₂S

[75] Inventor: John H. Kolts, Ochelata, Okla.

[73] Assignee: Phillips Petroleum Company, Bartlesville, Okla.

[21] Appl. No.: 758,921

[22] Filed: Jul. 25, 1985

[51] Int. Cl.⁴ .............................................. C07C 4/02
[52] U.S. Cl. .................................. 585/651; 585/653; 585/661; 585/662
[58] Field of Search ............... 585/651, 653, 661, 662, 585/663

[56] References Cited

U.S. PATENT DOCUMENTS

| | | | |
|---|---|---|---|
| 2,122,787 | 7/1938 | Tropsch | 585/663 |
| 2,269,028 | 1/1942 | Liedholm et al. | 585/663 |
| 2,415,477 | 2/1947 | Folkins et al. | 585/651 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,172,854 | 10/1979 | Ellis et al. | 585/663 |
| 4,471,151 | 9/1984 | Kolts | 585/651 |

FOREIGN PATENT DOCUMENTS

| | | | |
|---|---|---|---|
| 47-42703 | 12/1972 | Japan | 585/653 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

Primary Examiner—John Doll
Assistant Examiner—Lance Johnson
Attorney, Agent, or Firm—C. F. Steininger

[57] ABSTRACT

Feed hydrocarbons comprising propane and butanes are cracked to selectively maximize the production of ethylene or propylene by contacting the feed hydrocarbons with a cracking catalyst, adapted to convert the feed hydrocarbons to less saturated hydrocarbons, under conditions sufficient to thus crack the feed hydrocarbons, to thereby selectively maximize the production of ethylene, and, at least intervally, hydrogen sulfide or a hydrogen sulfide precursor is added to the feed hydrocarbons to thereby maximize the production of propylene. Preferred catalysts which may be utilized in the process and which are highly selective to the production of ethylene, as opposed to propylene, (in the absence of hydrogen sulfide or hydrogen sulfide precursor) include mixed oxides of manganese and magnesium, mixed oxides of manganese and Lanthanum Series metal and/or niobium, mixed oxides of iron and magnesium and mixed oxides of iron and Lanthanum Series metal and/or niobium. The effective life of the catalyst, particularly for the selective production of ethylene, is increased by carrying out the process in the presence of steam. When the catalyst contains manganese, the steam is optional whereas, when the catalyst contains iron, the steam is essential. The life of the magnesium based catalysts as well as their selectivity, particularly to ethylene, can also be extended by adding small promoting amounts of oxides of calcium, strontium, barium, tin, antimony, silicone, aluminum, titanium and/or chromium. All of the above promoters are useful in the iron/magnesium catalysts except the calcium, strontium, barium, tin and antimony. Only chromium is useful as a promoter for the Lanthanum Series and niobium based catalysts.

16 Claims, No Drawings

PROPYLENE AND ETHYLENE SELECTIVITY WITH H₂S

The present invention relates to the cracking of propane and butanes to ethylene and propylene. In a more specific aspect, the present invention relates to a method for cracking of propane and butanes to selectively maximize production of either ethylene or propylene.

BACKGROUND OF THE INVENTION

Olefins, such as ethylene and propylene, have become major feedstocks in the organic chemical and petrochemical industries. While the requirements for ethylene, as a feedstock, is about double that for propylene, fluctuations in the demand for these two materials make it desirable to produce one rather than the other, as required by market demands. Consequently, it would be highly desirable to be able to maximize the production of ethylene, as opposed to propylene, or vice versa, utilizing the same system in the same mode of operation, particularly utilizing a catalyst.

Numerous suggestions have been made for the production of ethylene and propylene from various feedstocks and by a wide variety of processes.

At the present time ethylene and propylene are produced almost exclusively by dehydrogenation or thermal cracking of ethane and propane, naphtha and, in some instances, gas oils. About 75 percent of the ethylene and propylene currently produced in the United States is produced by steam cracking of ethane and higher normally gaseous hydrocarbons derived from natural gas, since natural gas contains from about 5 volume percent to about 60 volume percent of hydrocarbons other than methane. However, in most instances, the content of ethane and higher normally gaseous hydrocarbons in natural gas is less than about 25 percent and usually less than about 15 percent. Consequently, these limited quantities of feedstocks, which are available for the production of ethylene and propylene, must be utilized efficiently. Unfortunately, these processes result in low conversions to olefins and selectively to ethylene, as opposed to propylene, is usually poor. In addition, relatively severe conditions, particularly temperatures in excess of about 1,000° C., are required and such processes are highly energy intensive.

In order to reduce the severity of the conditions and, more importantly, to improve the conversion of normally gaseous feedstocks to ethylene and propylene, numerous processes involving the use of solid contact materials have been proposed. Some of these proposals utilize inert solid contact materials in order to improve contact between the feed hydrocarbons and steam and also to maintain a more even temperature throughout the zone of reaction. In other instances, the solid contact material is catalytic in nature. Such use of solid contact materials, particularly catalysts, have resulted in modest improvements in conversion to ethylene and propylene but the selectivity is improved very little. It is, therefore, highly desirable that improved catalytic processes be developed, particularly processes which increase the selectivity to ethylene and propylene. However, little is understood concerning the manner in which such catalysts function, why certain components are effective while similar components are ineffective and why certain combinations of components are effective and other combinations are not. Obviously, a number of theories have been proposed by workers in the art, but this only adds to the confusion, since it appears that each theory explains why a particular contact material works well but does not explain why similar catalytic materials do not work and why other dissimilar materials are effective. As a result the art of catalytic conversion of hydrocarbons to olefins remains highly unpredictable.

As previously indicated, it would be highly desirable to be able to utilize the same equipment and the same mode of operation to maximize either ethylene or propylene production, as market conditions dictate. However, this is complicated by a number of factors. One difficulty is that both thermal and catalytic processes, in the past, produce substantially larger volumes of propylene than ethylene. Where a catalyst is utilized, it is necessary, in most instances, to change catalysts in order to maximize ethylene and propylene production as desired. It is also possible to shift production from ethylene to propylene or vice versa by the addition of catalyst-poisoning materials to the feed. However, such added materials have a tendency to permanently damage the catalyst, in many cases, to the extent that replacement is necessary. Accordingly, it is generally not possible to repeatedly change from the maximization of ethylene to propylene and vice versa.

SUMMARY OF THE INVENTION

It is therefore an object of the present invention to provide an improved method for cracking propane and butanes to produce ethylene and propylene, which overcomes the above and other disadvantages of the prior art. Another object of the present invention is to provide an improved method for the cracking of propane and butanes to selectively maximize the production of ethylene or propylene. Still another object of the present invention is to provide an improved method for the cracking of propane and butanes to selectively maximize the production of ethylene or propylene, in the presence of a catalytic material. Yet another object of the present invention is to provide an improved method for cracking propane and butanes, in the presence of catalyst, which significantly increases the production of ethylene, as opposed to propylene. Another and further object of the present invention is to provide an improved method for the cracking of propane and butanes, in the presence of catalyst, which produces substantially increased amounts of ethylene, as opposed to propylene, but can be utilized to increase the production of propylene, as opposed to ethylene, without noticeable deactivation or damage to the catalyst.

These and other objects of the present invention will be apparent from the following description.

It has been found, in accordance with the present invention, that propane and butanes can be cracked to selectively maximize the production of ethylene or propylene by contacting the feed hydrocarbons with a cracking catalyst, adapted to convert the feed hydrocarbons to less saturated hydrocarbons, under conditions sufficient to thus crack the feed hydrocarbons, whereby the production of ethylene is maximized and to then add hydrogen sulfide or a hydrogen sulfide precursor, without changing catalyst or the conditions of operation, whereby the production of propylene is maximized. Preferred catalyst compositions which selectively produce ethylene, as opposed to propylene, in the absence of hydrogen sulfide, include oxides of manganese and magnesium, oxides of manganese and Lanthanum Series metals and/or niobium, oxides of iron and magnesium and oxides of iron and Lanthanum Series metals and/or niobium. The life of the catalyst can be extended and the selectivity to ethylene improved by carrying out the reaction in the presence of steam. In addition, the life of the catalyst may be extended and the selectivity to ethylene increased by the addition of certain promoting metal oxides to the basic catalysts.

DETAILED DESCRIPTION OF THE INVENTION

The present invention provides a convenient method for catalytically cracking propane and butanes to produce ethylene and propylene, in which the operation can be modified to repeatedly switch from the maximization of ethylene production to the maximization of propylene production, without noticeable deterioration or damage to the catalyst. In a preferred embodiment of the present invention, a particular group of catalysts are utilized, which produce substantially greater quantities of ethylene, as opposed to propylene, than conventional catalysts yet can be so converted to the maximization of propylene production, without deterioration or damage to the catalyst's ability to again produce substantially larger quantities of ethylene, as opposed to propylene.

The hydrocarbon feed, in accordance with the present invention, can include any normally gaseous hydrocarbon stream containing significant amounts of propane and butanes. The presence of other normally gaseous components or even normally liquid components, which vaporize at operating conditions, are not detrimental to the process. For example, if significant amounts of isobutanes are present, as opposed to n-butane, there will be some increase in the production of butenes and, if ethane is present, there appears to be little effect on product distribution. Components other than hydrocarbons are also generally not detrimental to the process. The primary criteria in all cases is the cost or difficulty of separating inert materials or the products of components other than propane and butanes from the desired ethylene and propylene and whether such separation is less costly and/or less difficult before or after conduct of the process. Suitable feedstocks for the process of the present invention can be obtained from any source including natural gas, refinery off-gases and the like. However, the most convenient and abundant source is propane and butanes streams recovered during the processing of natural gas to produce pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6+$ hydrocarbons or natural gasoline), then $C_5$, followed by $C_4$, then $C_3$, and finally, $C_2$ hydrocarbons, by cooling to successively lower temperatures, with separation or fractionation of condensed liquid from condensed vapor between cooling stages. Thus, individual streams, predominating in an individual hydrocarbon such as $C_5$, $C_4$, $C_3$ and $C_2$, can be obtained or streams predominating in combinations of these individual hydrocarbons can be recovered. Accordingly, the thus separated propane stream or the thus separated butanes stream can be utilized as a feed hydrocarbon for the present invention or a stream predominating the mixture of propane and butanes can be utilized. Obviously, the latter would eliminate the necessity of one stage of cooling and separation in a natural gas processing system.

In addition to hydrogen sulfide, a large group of hydrogen sulfide precursors may be utilized, in accordance with the present invention. In general such hydrogen sulfide precursors include low molecular weight sulfur containing compounds. Suitable examples, include, mercaptans such as methyl, ethyl, propyl, isopropyl etc., sulfides such as dimethyl, diethyl, diisopropyl etc. and disulfides including dimethyl, diethyl, diisopropyl etc. Other suitable sulfur containing compounds and hydrogen sulfide precursors which perform the same function will be apparent to one skilled in the art.

The effectiveness of a sulfur containing compound such as hydrogen sulfide is quite surprising, since these materials are known in the art to permanently poison cracking catalysts, thereby reducing there activity or rendering them useless for their intended purpose. However, it has been found, in accordance with the present invention, that hydrogen sulfide and hydrogen sulfide precursors as set forth above, do not effect the activity of the catalyst of the present invention and, as will be shown hereinafter, hydrogen sulfide can be repeatedly added to the feed hydrocarbons to increase the selectivity to propylene production and discontinued to increase the selectivity to ethylene production, without any noticeable reduction in the ability of the catalyst to maximize ethylene production.

In the preferred embodiment of the present invention the cracking catalyst is selected from four catalyst systems which are highly effective in maximizing the production of ethylene, as opposed to propylene. While each of these catalyst systems possesses its own peculiarities, all are substantially superior to prior art systems, for selectively producing ethylene. These catalyst systems, include:

(a) a catalyst composition comprising: (1) at least one oxide of manganese and (2) at least one oxide of magnesium;

(b) a catalyst composition comprising: (1) at least one oxide of manganese and (2) at least one oxide of at least one metal selected from the group consisting of Lanthanum Series metals and niobium;

(c) a catalyst composition comprising: (1) at least one oxide of iron and (2) at least one oxide of magnesium; and (d) a catalyst composition comprising: (1) at least one oxide of iron and (2) at least one oxide of at least one metal selected from the group consisting of Lanthanum Series metals and niobium.

In general the oxide of manganese or the oxide of iron will be present in a minor proportion and the oxide of magnesium, the oxide of Lanthanum Series metals and the oxide of niobium will be present in major proportions.

Suitable amounts of oxides of manganese or oxides of iron are from about 0.1 to about 30 wt. %, expressed in terms of elemental metal based on the total weight of the catalytic mixture. Preferred manganese or iron contents are between about 0.5 and about 10 wt. %, expressed in terms of elemental metal based on total weight of the catalyst mixture.

During operation, in accordance with the present invention, it has been found that small amounts of the feed hydrocarbons are converted to coke, which is then deposited upon the catalyst and contributes to a decline in catalyst activity, particularly its selectivity to ethylene production. Accordingly, it is desirable to periodically regenerate the catalyst by conventional techniques of carbon removal, such as treatment with an oxygen-containing gas, such as air. During such regeneration, it may also be desirable to use inert gas or stream dilution to control burn-off temperatures, as is also well known to those skilled in the art. In general, it has been found that such regeneration is desirable at about 10 minute intervals. However, in accordance with further embodiments of the present invention, it has been found that the effective life of the catalyst for the selective production of ethylene can be significantly extended.

One method of extending the activity of the catalyst, for selective ethylene production, is to carry out the process in the presence of steam. In this respect, it has also been found that, while the use of steam is optional when the catalyst systems containing oxides of manganese are utilized, such use of steam is essential to the process when catalyst containing oxides of iron are utilized. Where oxides of iron are present in the catalyst it has been found that the selectivity to ethylene rapidly deteriorates and eventually the iron oxides are reduced to metallic iron which is wholly ineffective as a catalyst. The suitable steam/hydrocarbon mole ratios are between about 0 and about 10/1 for iron-free catalysts and about 0.1 to about 10/1 for iron-containing catalysts, and preferably between about 0.5 and about 5/1.

In accordance with a further preferred embodiment of the present invention, it has also been found that the addition of small amounts of other metallic oxides, hereafter referred to as the promoters, are also highly effective in extending the period over which the catalysts will selectively produce ethylene, as opposed to propylene. Some of these promoters are effective for some of the catalysts but are ineffective or detrimental to others. The effective promoter-catalyst combinations may be summarized as follows.

The Mn/MgO catalyst can be improved by the addition of small amounts of oxides selected from the group consisting of calcium, strontium, barium, tin and antimony. Of this group calcium is preferred. This catalyst may also be improved by the addition of at least one oxide of an element selected from the group consisting of silicon, aluminum and titanium. Combinations of silicon, aluminum and titanium and calcium, strontium, barium, tin and antimony may also be utilized. Finally, this catalyst can be improved by the addition of promoting amounts of at least one oxide of chromium. Chromium may also be utilized in combination with the calcium, strontium, barium, tin and antimony promoters.

The Mn/Lanthanum Series or niobium catalysts may also be improved by the addition of at least one oxide of chromium.

The Fe/MgO catalysts are improved by addition of at least one oxide of an element selected from the group consisting of silicon, aluminum and titanium or at least one oxide of chromium.

The Fe/Lanthanum Series and niobium catalysts may contain promoting amounts of at least one oxide of chromium.

Suitable amounts of subject promoters are between about 0.1 and about 30 wt. %, expressed in terms of the element based on the total weight of the catalyst composition, and preferably between about 1 and about 15 wt. %. Preferred amounts of the promoters are between about 2 and about 6 wt. %. While the content of manganese and/or iron may be between about 0.1 and about 30 wt. %, when the promoters are present this amount will generally be reduced. When in combination with the promoters, a preferred range is between about 0.2 and about 10 weight percent, expressed in terms of the elements based on the total weight of the catalyst composition.

The method of catalyst preparation does not appear to be critical, so long as the desired final composition of the component metal oxides is obtained. Suitable methods of preparation include slurry blending, solution blending, dry blending, impregnation and co-precipitation, all of which are well known to those skilled in the art. A convenient method is to add metal solids, such as, $MgO$ or $Mg(OH)_2$, to a blending apparatus along with a aqueous solution of a salt of the minor component, for example, $Mn(NO_3)_2 \cdot 6H_2O$, and mixing for several minutes, for example, two to five minutes, to form a thick slurry. In the interest of economy, excess water should be avoided. Additional catalyst components or promoters may also be added as desired as either solids or solutions before or during blending. Generally, the catalyst composition is formed by the slurry method and small amounts of promoters are added by impregnation as a solution of, for example, nitrates. The resulting slurry is then dried in air by conventional means, at about 100° C. to 150° C., calcined for about 4 hours, at about 750° C. to 800° C., and then ground, sieved and, optionally, pelleted or otherwise sized by means well known in the art.

The process of the present invention can be carried out in fixed, moving, fluidized, ebulating or entrained bed reactors. For experimental purposes and, obviously, to permit accurate measurement and precise control of the process variables, the runs hereafter set forth in the example were conducted in a fixed bed reactor.

Following preparation of the catalyst, the catalyst may be prepared for use by purging with an inert gas, such as nitrogen. Normally, the catalyst would be disposed in the reactor, brought up to reaction temperature by preheating with air, then purged with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher states of oxidation of manganese and/or iron and, thereby, reduces initial carbon oxide formation.

With the exception of the temperature of operation, the operating conditions of the process, in accordance with the present invention, do not appear to be highly critical. Accordingly, the following conditions of operation are those found effective and preferred.

The hydrocarbon gas hourly space velocity (GHSV) may range from 100 to about 3,000 but is preferably between about 500 to about 1,000.

The operating pressure may be between about 0.1 and about 100 psia and is preferably between about 1 and about 60 psia.

The temperature of operation appears to be significant in the conversion of feed hydrocarbons to olefins and particularly in improving the selectivity to ethylene. Suitable temperatures range between about 550° C.

and about 850° C. with the preferred range being between about 650° C. and about 775° C.

and the selectivity as mol % n-butane converted to the particular product.

TABLE 1

| No of Cycles | H₂S Addn. | Conv. | Selectivity C₂= | C₃= | C₂ | $\frac{C_2^= + C_2}{C_3^=}$ | $\frac{C_2^=}{C_3^=}$ | Average $\frac{C_2^=}{C_3^=}$ w/o H₂S | Average $\frac{C_2^=}{C_3^=}$ w H₂S |
|---|---|---|---|---|---|---|---|---|---|
| 3 | No | 65 | 35 | 22 | 18 | 2.41 | 1.59 | | |
| 7 | Yes | 68 | 19 | 38 | 10 | 0.76 | 0.50 | | |
| 18 | No | 64 | 37 | 22 | 19 | 2.55 | 1.68 | | |
| 21 | Yes | 65 | 20 | 41 | 9 | 0.71 | 0.49 | | |
| 31 | No | 72 | 35 | 18 | 22 | 3.17 | 1.94 | | |
| | | | | | | | | 1.74 | 0.50 |
| 1 | No | 62 | 34 | 27 | 15 | 1.81 | 1.26 | | |
| 35 | Yes | 66 | 17 | 42 | 8 | 0.59 | 0.40 | | |
| 53 | No | 57 | 34 | 28 | 16 | 1.79 | 1.21 | | |
| 56 | Yes | 58 | 18 | 42 | 8 | 0.62 | 0.43 | | |
| 70 | No | 60 | 33 | 28 | 16 | 1.75 | 1.18 | | |
| 74 | Yes | 64 | 19 | 41 | 9 | 0.68 | 0.46 | | |
| 88 | No | 51 | 32 | 30 | 14 | 1.60 | 1.07 | | |
| 92 | Yes | 58 | 19 | 42 | 8 | 0.64 | 0.45 | | |
| | | | | | | | | 1.18 | 0.44 |

In the operation of the process, the process will be carried out in the absence of hydrogen sulfide or a hydrogen sulfide precursor. Under these conditions, the process is selective to the production of ethylene, as opposed to propylene, and will be run in this mode a major part of the time, since propylene is also produced in lesser amounts and the market demand for ethylene exceeds that for propylene. However, at least intervally, either because of market demands or for some other reason, it is desirable to maximize the production of propylene. Accordingly, this is accomplished, simply by adding appropriate amounts of hydrogen sulfide or a hydrogen sulfide precursor to the feed hydrocarbons. The range of useful hydrogen sulfide concentrations is between about 0.1 and about 30 mol percent, with a preferred concentration being between about 0.1 and about 5 mol percent. Once a sufficient volume of propylene has been produced in this manner, the selective production of ethylene, as opposed to propylene, can be resumed simply by discontinuing the introduction of hydrogen sulfide or hydrogen sulfide precursor. Such interval maximization of propylene production can be repeated in the same manner, as necessary or desired, and, as previously indicated, the activity of the catalyst and the selective production of ethylene is unaffected.

The nature and advantages of the present invention are illustrated by the following example.

A series of tests was made in which n-butane was cracked over a 3% Ca/5% Mn/MgO catalyst at 700° C. and utilizing a 1/1 steam/hydrocarbon ratio. The catalysts was utilized for a number of process cycles, of 30 to 60 minutes duration, with intermittent cycles in which 1 percent (molar) hydrogen sulfide was included in the feed. The catalyst was conventionally regenerated using air and steam following each cycle. Typical results were set forth in the following table in which the cycle numbers represent, for example, 3 ethylene production—regeneration cycles (without hydrogen sulfide), then 7 propylene production—regeneration cycles (in the presence of hydrogen sulfide), then 18 ethylene production-regeneration cycles (without hydrogen sulfide), etc. In the second series of runs, each cycle was 30 minutes in length. 25 cc of the catalyst were disposed in a fixed bed quartz reactor. Snap samples of product were taken and analyzed by gas chromatography. The conversion is expressed in mol % of n-butane converted It is to be noted from the above data that at each interval in which hydrogen sulfide was used the selectivities to ethylene and ethane were suppressed by about 50 percent and the selectivity to propylene was increased by about 40 to almost 100 percent. In all cases, when addition of H₂S was discontinued, the product distribution returned almost immediately to what it was before H₂S addition.

While specific materials, conditions of operation, modes of operation and equipment have been referred to herein, it is to be recognized that these and other specific recitals are for illustrative purposes and to set forth the best mode only and are not to be considered limiting.

That which is claimed is:

1. A method for cracking feed hydrocarbons comprising at least one of propane and butanes to produce less saturated hydrocarbon products and selectively maximize the content of one of ethylene and propylene in said less saturated hydrocarbon products, comprising:
   (a) contacting said feed hydrocarbons with a cracking catalyst selected from the group consisting of:
      (1) a catalyst composition, consisting essentially of: 0.1 to 30 wt. % of (A) at least one oxide of manganese and the balance of (B) at least one oxide of magnesium;
      (2) a catalyst composition, consisting essentially of: 1 to 15 wt.% of (A) at least one oxide of one metal selected from the group consisting of calcium, strontium, barium, tin and antimony, 0.1 to 30 wt.% of (B) at least one oxide of manganese and the balance of (C) at least one oxide of magnesium;
      (3) a catalyst composition, consisting essentially of: 1 to 15 wt.% of (A) at least one oxide of a metal selected from the group consisting of silicon, aluminum and titanium, 0.1 to 30 wt.% of (B) at least one oxide of manganese and the balance of (C) at least one oxide of magnesium;
      (4) a catalyst composition, consisting essentially of: 1 to 15 wt.% of (A) at least one oxide of a metal selected from the group consisting of calcium, strontium, barium, tin and antimony, 1 to 15 wt.% of (B) at least one oxide of a metal selected from the group consisting of silicon, aluminum and titanium, 0.1 to 30 wt.% of (C) at least one oxide of manganese and the balance of (D) at least one oxide of magnesium;

(5) a catalyst composition, consisting essentially of: 1 to 15 wt.% of (A) at least one oxide of chromium, 0.1 to 30 wt.% of (B) at least one oxide of manganese and the balance of (C) at least one oxide of magnesium; and (6) a catalyst composition, consisting essentially of: 1 to 15 wt.% of (A) at least one oxide of chromium, 1 to 15 wt.% of (B) at least one oxide of a metal selected from the group consisting of calcium, strontium, barium, tin and antimony, 0.1 to 30 wt.% of (C) at least one oxide of manganese and the balance of (D) at least one oxide of magnesium, said amounts being expressed in terms of wt.% of the elemental metal based on the total weight of the catalyst;

in the absence of significant amounts of hydrogen sulfide and hydrogen sulfide precursors and under predetermined conditions to produce said less saturated hydrocarbon products containing substantially greater quantities of ethylene than propylene; and (b) at least intervally, adding a material selected from the group consisting of hydrogen sulfide and hydrogen sulfide precursors to said feed hydrocarbons, in the presence of said cracking catalyst, under said predetermined conditions to produce said less saturated hydrocarbons containing substantially increased quantities of propylene and decreased quantities of ethylene.

2. A method in accordance with claim 1 wherein addition of a material selected from the group consisting of hydrogen sulfide and hydrogen sulfide precursors is discontinued and step (a) is repeated, at least once.

3. A method in accordance with claim 1 wherein the feed hydrocarbons comprise propane.

4. A method in accordance with claim 1 wherein the feed hydrocarbons comprise butanes.

5. A method in accordance with claim 1 wherein the feed hydrocarbons comprise a mixture of propane and butanes.

6. A method in accordance with claim 1 wherein the temperature of contacting is between about 550° C. and about 850° C.

7. A method in accordance with claim 1 wherein the contacting is carried out in the presence of steam.

8. A method in accordance with claim 7 wherein the steam/feed hydrocarbons mol ratio is less than about 10/1.

9. A method in accordance with claim 1 wherein the material selected from the group consisting of hydrogen sulfide and hydrogen sulfide precursors is added in the amount of about 0.1 to 30 mol percent, expressed in terms of hydrogen sulfide.

10. A method in accordance with claim 1 wherein the catalyst consists essentially of at least one oxide of manganese and at least one oxide of magnesium.

11. A method in accordance with claim 1 wherein the catalyst consists essentially of at least one oxide of a metal selected from the group consisting of calcium, strontium, barium, tin and antimony, at least one oxide of manganese and at least one oxide of magnesium.

12. A method in accordance with claim 11 wherein the metal selected from the group consisting of calcium, strontium, barium, tin and antimony is calcium.

13. A method in accordance with claim 1 wherein the catalyst consists essentially of at least one oxide of a metal selected from the group consisting of silicon, aluminum and titanium, at least one oxide of manganese and at least one oxide of magnesium.

14. A method in accordance with claim 1 wherein the catalyst consists essentially of at least one oxide of a metal selected from the group consisting of calcium, strontium, barium, tin and antimony, at least one oxide of a metal selected from the group consisting of silicon, aluminum and titanium, at least one oxide of manganese and at least one oxide of magnesium.

15. A method in accordance with claim 1 wherein the catalyst consists essentially of at least one oxide of chromium, at least one oxide of manganese and at least one oxide of magnesium.

16. A method in accordance with claim 1 wherein the catalyst consists essentially of at least one oxide of chromium, at least one oxide of a metal selected from the group consisting of calcium, strontium, barium, tin and antimony, at least one oxide of manganese and at least one oxide of magnesium.

* * * * *